US00PP34741P2

(12) United States Plant Patent
van Sambeek

(10) Patent No.: US PP34,741 P2
(45) Date of Patent: Nov. 15, 2022

(54) ***PHLOX* PLANT NAMED 'DOPHLOFLAWA'**

(50) Latin Name: *Phlox paniculata*
Varietal Denomination: Dophloflawa

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/695,257

(22) Filed: Mar. 15, 2022

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 6/70; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phlox* plant named 'Dophloflawa', characterized by its upright and uniform plant habit; moderately vigorous growth habit and moderate growth rate; freely branching habit; early and freely flowering habit; large red-colored flowers with reddish purple-colored centers; and good container and garden performance.

1 Drawing Sheet

Botanical designation: *Phlox paniculata.*
Cultivar denomination: 'DOPHLOFLAWA'.

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Oct. 21, 2021, application number 2021/2620. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phlox* plant, botanically known as *Phlox paniculata* and hereinafter referred to by the name 'Dophloflawa'.

The new *Phlox* plant is a product of a planned breeding program conducted by the Inventor in Aalsmeer, The Netherlands. The objective of the breeding program was to create new early and freely-flowering *Phlox* plants with attractive flower color.

The new *Phlox* plant originated from an open-pollination in July, 2014 of a proprietary selection of *Phlox paniculata* identified as code number PA13-000032-002, not patented, as the female, or seed, parent with an unknown selection of

*Phlox paniculata* as the male, or pollen, parent. The new *Phlox* plant was discovered and selected by the Inventor as a single flowering plant within the progeny of the stated open-pollination in a controlled environment in Aalsmeer, The Netherlands in July, 2015

Asexual reproduction of the new *Phlox* plant by vegetative cuttings in a controlled environment in Aalsmeer, The Netherlands since March, 2016 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Dophloflawa'. These characteristics in combination distinguish 'Dophloflawa' as a new and distinct *Phlox* plant:

1. Upright and uniform plant habit.
2. Moderately vigorous growth habit and moderate growth rate.
3. Freely branching habit.
4. Early and freely flowering habit.
5. Large red-colored flowers with reddish purple-colored centers.
6. Good container and garden performance.

Plants of the new *Phlox* differ from plants of the female parent selection primarily in flower color as petal lobes of plants of the new *Phlox* have red-colored flowers with reddish purple-colored centers whereas plants of the female parent selection have red-colored flowers with pink-colored centers.

Plants of the new *Phlox* can be compared to plants of *Phlox paniculata* 'Sweet Summer Candy', not patented. In side-by-side comparisons, plants of the new *Phlox* and 'Sweet Summer Candy' differ in the following characteristics:

1. Plants of the new *Phlox* have smaller flowers than plants of 'Sweet Summer Candy'.
2. Plants of the new *Phlox* have red-colored flowers with reddish purple-colored centers whereas plants of 'Sweet Summer Candy' have pink-colored flowers.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant. The photograph comprises a side perspective view of typical flowering plant of 'Dophloflawa' grown in a container.

DETAILED BOTANICAL DESCRIPTION

The aforementioned photograph and following observations, measurements and values describe plants grown during the early summer in 17-cm containers initially in a glass-covered greenhouse and finished in an outdoor nursery in Aalsmeer, The Netherlands and under cultural practices typical of commercial *Phlox* production. During the production of the plants, day temperatures averaged 21° C. and night temperatures averaged 15° C. Plants were pinched one time one week after planting rooted young plants and were 29 weeks old when the photograph and the description were taken. In the following description, color references are made to The Royal Horticultural Society Colour Chart, Second Edition, except where general terms of ordinary dictionary significance are used.

Botanical classification: *Phlox paniculata* 'Dophloflawa'.

Parentage:

*Female, or seed, parent*.—Proprietary selection of *Phlox paniculata* identified as code number PA13-000032-002, not patented.

*Male, or pollen, parent*.—Unknown selection of *Phlox paniculata*, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Thick, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright and uniform plant habit; moderately vigorous growth habit and moderate growth rate.

*Plant height*.—About 49 cm.

*Plant width (spread)*.—About 47 cm.

*Lateral branches*.—Branching habit: Relatively freely branching habit; about seven primary branches each with about two secondary branches. Length: About 44 cm. Diameter: About 5 mm. Internode length: About 2.5 cm. Strength: Strong. Aspect: Upright to about 30° from vertical. Texture and luster: Pubescent; glossy. Color, developing and developed: Close to 143A.

Leaf description:

*Arrangement*.—Opposite, simple; decussate and sessile.

*Length*.—About 15 cm.

*Width*.—About 4 cm.

*Shape*.—Lanceolate.

*Apex*.—Acuminate.

*Base*.—Obtuse.

*Margin*.—Entire.

*Texture and luster, upper and lower surfaces*.—Smooth, glabrous; semi-glossy.

*Venation pattern*.—Pinnate, reticulate.

*Color*.—Developing leaves, upper surface: Close to 137A. Developing leaves, lower surface: Close to 138A. Fully expanded leaves, upper surface: Close to 147A; venation, close to 144A. Fully expanded leaves, lower surface: Close to 138A; venation, close to 145C.

Flower description:

*Flower type and flowering habit*.—Single rotate and salverform flowers arranged in compound terminal and lateral panicles; flowers face mostly upright to outwardly depending on position on inflorescence; freely flowering habit with about 20 flowers per inflorescence and about 670 flowers developing per plant during the flowering season.

*Fragrance*.—Slightly fragrant; sweet, pleasant.

*Natural flowering season*.—Early flowering habit; plants begin flowering about twelve weeks after planting; plants flower in July in the garden in The Netherlands; flowers not persistent.

*Flower buds*.—Height: About 3 cm. Diameter: About 7 mm. Shape: Conical. Texture and luster: Smooth, glabrous; matte. Color: Close to 62A.

*Inflorescence height*.—About 11 cm.

*Inflorescence diameter*.—About 12.5 cm.

*Flower diameter*.—About 3.2 cm.

*Flower depth*.—About 2.5 cm.

*Flower throat diameter*.—About 5 mm.

*Flower tube length*.—About 1.2 cm.

*Flower diameter, proximally*.—About 3 mm.

*Petals*.—Quantity per flower: Typically five in a single whorl; petals fused at the base into a narrow tube. Lobe length: About 1.5 cm. Lobe width: About 1.8 cm. Lobe shape: Obovate. Lobe apex: Rounded. Lobe margin: Entire, not undulate. Lobe texture and luster, upper and lower surfaces: Smooth, glabrous; matte. Throat texture and luster: Smooth, glabrous; matte. Tube texture and luster: Pubescent; matte. Color: Lobe, when opening, upper surface: Close to 52A; towards the throat, close to 74A. Lobe, when opening, lower surface: Close to 62A. Lobe, fully opened, upper surface: Close to 52A; towards the throat, close to 74A; venation, close to 52A; color does not change with subsequent development. Lobe, fully opened, lower surface: Close to 65A; venation, close to 65A; color does not change with subsequent development. Throat: Close to 74A; venation, close to 74A. Tube: Close to 71A; venation, close to 71A.

*Sepals*.—Quantity per flower: Typically five in a single whorl, fused towards the base; calyx, tubular. Length: About 1.1 cm. Width: About 2 mm. Shape: Subulate. Apex: Acuminate. Margin: Entire. Texture and luster, upper surface: Pubescent; semi-glossy. Texture and luster, lower surface: Pubescent; glossy. Color: When opening, upper and lower surfaces: Close to 143A. Fully opened, upper and lower surfaces: Close to 143A.

*Peduncles*.—Length: About 7 mm. Diameter: About 2 mm. Strength: Weak. Aspect: About 45° from lateral branch axis. Texture and luster: Smooth, glabrous; glossy. Color: Close to 146A.

*Pedicels*.—Length: About 4 mm. Diameter: About 1 mm. Strength: Weak. Aspect: Up to 40° from peduncle axis. Texture and luster: Smooth, glabrous; glossy. Color: Close to 144A.

*Reproductive organs*.—Stamens: Quantity per flower: Typically five. Filament length: About 2 mm. Filament color: Close to 72A. Anther size: About 1 mm by 3 mm. Anther color: Close to 12C. Pollen amount: Scarce. Pollen color: Close to 158A. Pistils: Quantity per flower: One. Pistil length: About 2.6 cm. Stigma diameter: About 1 mm. Stigma shape: Three-parted. Stigma color: Close to 144B. Style length: About 2.1 cm. Style color: Close to 145A. Ovary color: Close to 145A.

*Seeds and fruits*.—To date, seed and fruit development have not been observed on plants of the new *Phlox*.

Garden performance: Plants of the new *Phlox* have been observed to have good garden performance and to tolerate rain, wind and temperatures ranging from about −37° C. to about 35° C.

Pathogen & pest resistance: To date, plants of the new *Phlox* have not been observed to be resistant to pathogens and pests common to *Phlox* plants.

It is claimed:

1. A new and distinct *Phlox* plant named 'Dophloflawa' as illustrated and described.

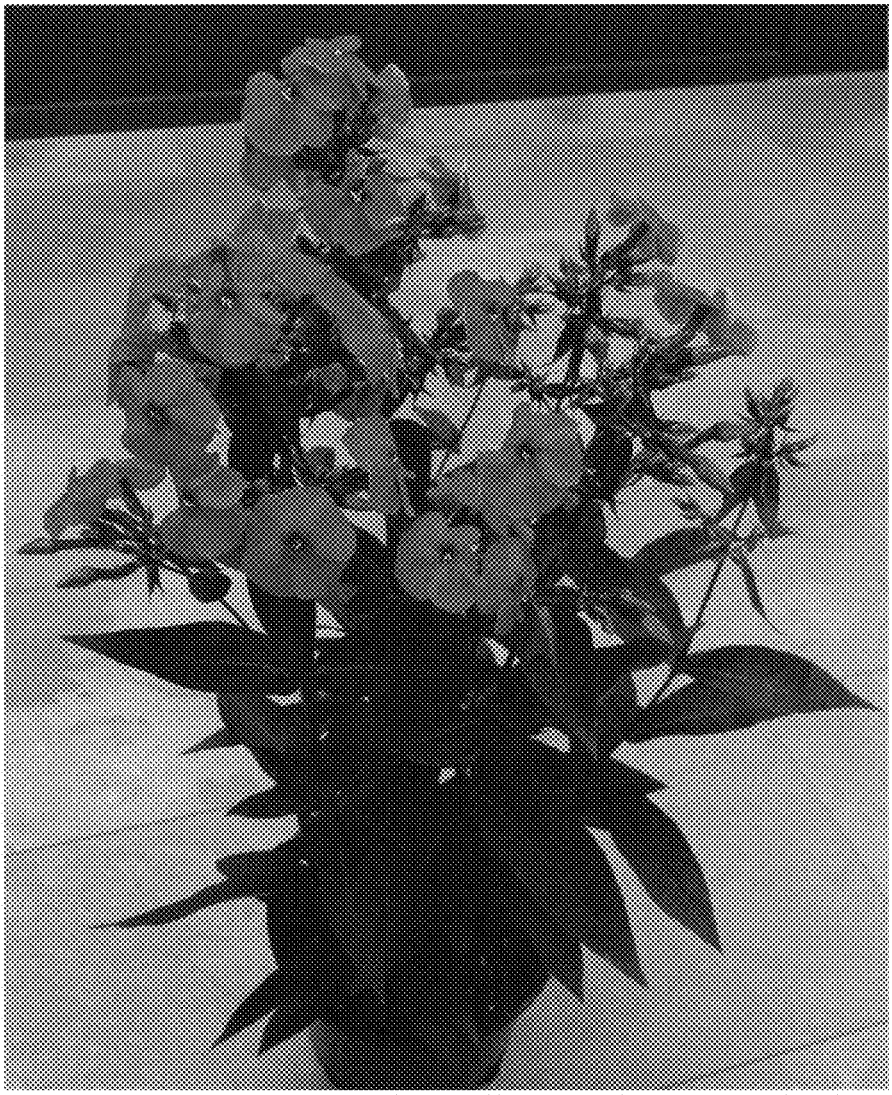

* * * * *